United States Patent [19]

Levine

[11] 4,316,882
[45] Feb. 23, 1982

[54] COMPOSITIONS FOR TESTING TO PREDICT AND/OR DIAGNOSE ALLERGY TO PENICILLINS

[76] Inventor: Bernard B. Levine, 210 Riverside Dr., New York, N.Y. 10025

[21] Appl. No.: 71,418

[22] Filed: Aug. 30, 1979

Related U.S. Application Data

[63] Continuation-in-part of Ser. No. 898,044, Apr. 20, 1978, Pat. No. 4,183,910.

[51] Int. Cl.³ .............................................. A61K 49/00
[52] U.S. Cl. ........................................ 424/9; 424/211; 424/270; 424/271; 548/201
[58] Field of Search ..................... 424/9, 211, 270, 271

[56] References Cited

U.S. PATENT DOCUMENTS 3,867,365  2/1975  Stahmann et al. ................. 424/9 X
3,979,508  9/1976  Stahmann et al. ....................... 424/9

OTHER PUBLICATIONS

Levine, *J. New England Medicine*, 275:1115, (1966).
Levine et al., *J. Clinical Investigation*, 47:556, (1968).
Levine et al., *J. of Allergy*, 43:231–244, (1969).

*Primary Examiner*—Natalie Trousof
*Assistant Examiner*—Vera C. Clarke
*Attorney, Agent, or Firm*—Sughrue, Mion, Zinn, Macpeak and Seas

[57] ABSTRACT

The invention relates to the testing of humans or other animals, such as horses, cattle or dogs, for allergic reaction or hypersensitivity to penicillins. The tests can be used both to predict and to diagnose allergy. The invention comprises new materials for use in minor determinant mixture (MDM) compositions and lyophilized, storage-stable MDM compositions and novel test methods employing such materials.

The new MDM materials are N-penicilloyl amines of an aliphatic amine or α-aminoacid having the following molecular structure:

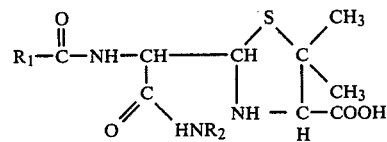

wherein:

$R_1$ = a side chain which defines the type of penicillin— e.g., where $R_1$ =

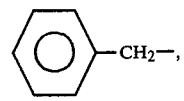

the new material is a derivative of benzylpenicillin; and $R_2$ is an alkyl group of $C_2$–$C_6$ length, preferably ethyl or propyl, or an aminoacid residue as described herein.

The tests are preferably carried out by applying solutions of the materials to the skin of the patient or other test animal and pricking or scratching the skin, or by injecting the materials intradermally, and then observing for wheal and flare reactions. The preferred test method comprises a two-solution test using a solution of the novel PPL preparations described in my copending U.S. Patent application Ser. No. 898,044 applied on or into one area of the patient's skin and a separate solution containing the new minor determinant material alone or as part of an MDM solution with other constituents applied on or into another area of the patient's skin.

3 Claims, No Drawings

COMPOSITIONS FOR TESTING TO PREDICT AND/OR DIAGNOSE ALLERGY TO PENICILLINS

This application is a continuation-in-part of my co-pending U.S. application Ser. No. 898,044, filed Apr. 20, 1978, now U.S. Pat. No. 4,183,910.

BACKGROUND OF THE INVENTION

1. Field of the Invention

The invention provides novel MDM materials and compositions and more sensitive tests for predicting and diagnosing allergy or hypersensitivity to penicillin in humans or other animals by skin testing with the improved MDM compositions of the invention.

2. Discussion of the Prior Art

Since the introduction of penicillins for therapeutic treatment of infections in humans and other animals, a variety of allergic reactions have been observed; the most serious of these reactions is anaphylactic shock, which is estimated to be the cause of several hundred deaths in the United States each year. The possibility of non-fatal anaphylaxis and urticarial reactions, which are much more common than fatal anaphylaxis, also is a matter of serious concern for the physician considering the treatment of a patient with penicillins.

Therefore, much research effort has been devoted to the development of reliable tests predictive of human allergic response or hypersensitivity to penicillin. As the result, certain skin tests have been described in the literature and are under study clinically. One such test generally involves scratching the skin in an area on which a test solution has been placed, or intradermally injecting the test solution, and observing for a positive reaction—i.e., a wheal-and-flare reaction around the scratch or injection sites formed within 15 minutes. More sensitive skin tests involve the intradermal injection of solutions containing (1) PPL and (2) MDM compositions.

The chemistry underlying the mechanism by which penicillin may trigger allergic reactions in humans and the details of the state of the art in "scratch" and "intradermal" skin tests is extensively set forth in the literature. The following are intended only as representative citations which provide useful technical background in the field of this invention:

"Immunological Mechanisms of Penicillin Allergy" B. B. Levine; J. New England Medicine, 275:1115 (1966)

"The Nature of the Antigen-Antibody Complexes Initiating the Specific Wheal-and-Flare Reaction in Sensitized Man" B. B. Levine, A. P. Redmond; J. Clinical Investigation, 47:556 (1968)

"Predictions of Penicillin Allergy by Immunological Tests" B. B. Levine, D. M. Zolov; J. of Allergy, 43:4:231 (1969)

"Drug Allergy" B. B. Levine; Reprint of Edited Remarks presented at seminar co-sponsored by Johns Hopkins U., Am. Acad. of Allergy and NIH (1971)

"Skin Rashes With Penicillin Therapy: Current Management" B. B. Levine; New England Journal of Medicine (1971)

"A Guide to Skin Testing for Penicillin Allergy" N. F. Adkinson, Jr., Resident and Staff Physician at Johns Hopkins U. (1977)

See also U.S. Pat. Nos. 3,867,365 and 3,979,508 issued to Stahmann and Wagle.

In prior studies, such as those cited above, it has also been shown that some patients who are given penicillin therapeutically develop IgE antibodies to certain haptens which are formed from the reaction of the penicillin with tissue proteins. These include the benzylpenicilloyl (BPO) hapten, whose structure is well known, and certain "minor determinant" haptens whose structures are not yet known.

IgE antibodies are known to mediate anaphylactic and other immediate allergic reactions to penicillin in man. These reactions are frequently severe, causing diffuse rash, difficulty in breathing, abdominal cramps and fainting, hypotension and arrythmia. They are capable of causing death due to cardiovascular collapse, ventricular arrythmia and/or respiratory obstruction.

Skin tests with various materials derived from penicillin have been shown to be positive in the presence of these IgE antibodies, and thus serve as a predictive test for severe penicillin allergy. The skin test compositions currently in use include benzylpenicilloyl-polylysine (BPL), which detects IgE antibodies specific for the BPO haptenic group, and the MDM, which detects IgE antibodies specific for the minor determinants.

Up to now, the MDM generally used has included combinations of two or more of benzylpencillin (PG), benzylpenicilloic acid (NaBPO), benzylpenilloic acid (POIC) and benzylpenicilloyl-amine (BPO-amine). The structures of the MDM materials used to date are set forth below:

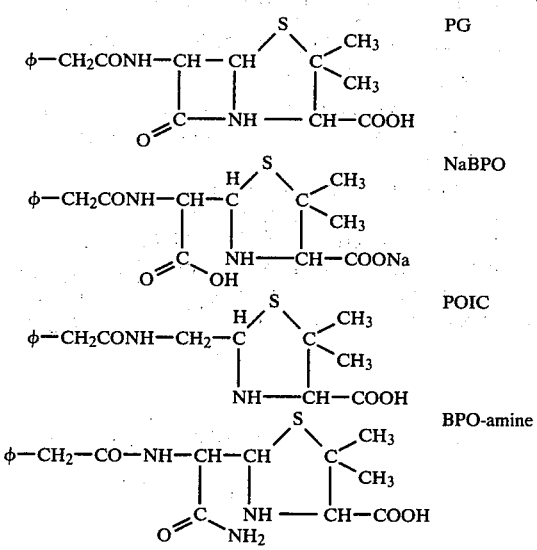

While intradermal testing using PPL and the MDM has proved very useful in predicting penicillin allergy, I have observed that with certain patients IgE antibodies induced by penicillin are undetected or only weakly detected by the MDM test compositions currently in use.

In accordance with my invention, I have observed that the addition of an N-penicilloyl-amine of an aliphatic amine or α-aminoacid, especially BPO-propyl amine or BPO-ethyl amine, to the MDM, greatly increases the intensity of the test.

In view of the possibly catastrophic consequences of observing a negative response in a patient who is actually allergic to penicillin, it is critical that the most sensitive and highly reliable allergy tests be made clinically available.

Further, the use of the most sensitive test is of importance when doing prick or scratch tests. These are much more convenient but less sensitive than intradermal tests. Thus, more sensitive test materials permit the use of a prick test.

Accordingly, the principal objective of my invention is to provide a more sensitive and reproducible skin test for penicillin allergy using improved MDM preparations. Another purpose is to provide novel MDM compounds and compositions, including storage-stable MDM materials, for use in skin testing for prediction or diagnosis of penicillin allergic reaction or hypersensitivity.

SUMMARY OF THE INVENTION

My invention comprises:

(1) New MDM materials. The materials are N-penicilloyl-amines of an aliphatic amine or α-aminoacid and MDM mixtures containing such materials. The N-penicilloyl amines or aminoacids may be α-diastereoisomers, other diastereoisomers or diastereoisomeric mixtures.

(2) Methods for skin testing for penicillin allergy or hypersensitivity using solutions containing the novel MDM materials independently or in a two-solution, combined test with the PPL preparations of my copending U.S. patent application Ser. No. 898,044. The new MDM materials may be used alone or as part of a multicomponent MDM. The skin tests may be prick, scratch or intradermal. Some of the compositions may also be useful for in vitro testing for penicillin allergy.

DETAILED DESCRIPTION OF THE INVENTION

My invention will be more fully appreciated in view of the following detailed description of certain preferred embodiments.

1. Preparation of MDM Materials

Improved penicillin allergy or hypersensitivity skin testing can be achieved by use of an MDM which comprises an N-penicilloyl amine of an aliphatic amine, such as N-propyl amine or ethyl amine, or of an α-aminoacid, such as α-aminobutyric acid, norvaline, glutamine, proline, etc., as a new ingredient of the MDM, in addition to penicilloic acid and penicillin. These new materials (the N-penicilloyl amines of aliphatic amines or α-aminoacids) detect IgE antibodies induced by penicillin which are undetected or only weakly detected by the currently utilized skin test materials. For example, Table II shows results of skin testing patients allergic to penicillin. Patients MB and CM gave more intense skin tests to BPO-ethyl amine and BPO-propyl amine than they did to the other minor determinant test materials. These BPO-alkyl amines do not reflect reactivity to either BPL or the other minor determinants, as there is no relationship between them. For example, patient CM was entirely negative to BPL while giving a positive reaction to BPO-ethyl amine and BPO-propyl amine. Note, also, positive reactions to BPO-propyl amine and BPO-ethyl amine associated with negative reactions to PG. Note that patients CM and MB gave stronger reactions to BPO-propyl amine and BPO-ethyl amine than to P/P (NaBPO plus POIC), while the reverse was true for patients LG and NT. Finally, note a lack of relationship between test intensities of BPO-amine and BPO-propyl amine.

The rationale for the use of a BPO-alkyl amine or aminoacid is that in some patients an important penicillin hapten or allergen may form from the reaction of penicillin with an amine or aminoacid present in blood plasma and tissue fluids. It has been hypothesized that NaBPO may become allergenic by first rearranging to benzylpenamaldic acid which can bind chemically to tissue proteins via mixed disulfide linkages to cysteine residues of protein.

Alternatively, benzylpenamaldic acid may degrade to benzylpenaldic acid (an aldehyde compound) which may react chemically with amino groups of protein binding via a Schiff base. The same sequence may be postulated for a penicilloyl-amine. Note that in both cases, the alkyl amine or aminoacid side chain would be an integral part of the haptenic group.

The alternatives which I have hypothesized are outlined in the following reactions:

2. Hypothetical Minor Haptenic Determinants

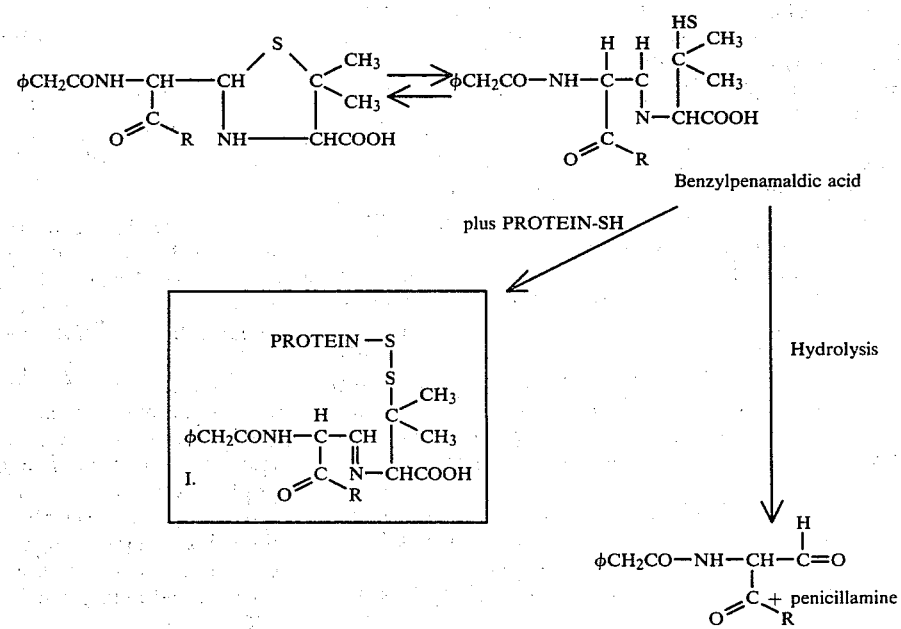

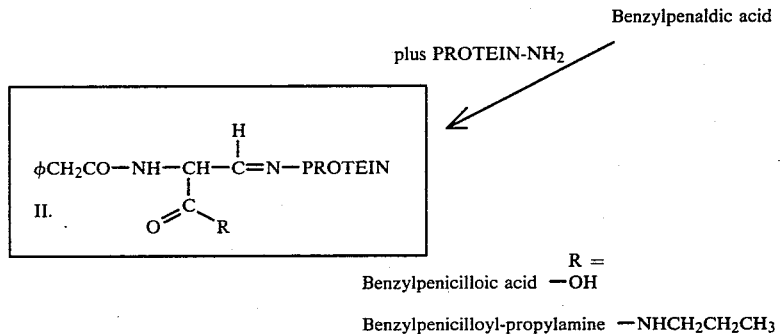

Benzylpenicilloic acid —OH

Benzylpenicilloyl-propylamine —NHCH₂CH₂CH₃

In vivo, some of the circulating penicillin hydrolyses to penicilloic acid, and some may react with amines or aminoacids circulating in the plasma to form BPO-alkyl amines or BPO-aminoacids. Further rearrangement and/or degradation of the BPO-amines and reaction of those products with proteins as described above would result in the formation of allergenic hapten-protein conjugates. Some individuals may mount an immune response to one or more of these haptens. Skin testing with NaBPO, POIC or BPO-amine (which lack the alkyl amine or aminoacid side chain in their structures) may fail to detect IgE antibodies directed against the BPO-alkyl amine or BPO-aminoacid hapten in some patients. In some patients, some cross-reactivity between NaBPO and the BPO-alkyl amine (or aminoacid) probably exists, but a considerable decrease in skin test reaction intensity would result. Thus, testing with low concentrations of NaBPO (or testing by prick test, which amounts to the same thing) would fail to detect sensitivity, while testing with BPO-alkyl amine or BPO-aminoacid in low concentration or by prick test would be more likely to detect that sensitivity. In my new test, I intend to use the prick test to test patients without past histories of penicillin allergy who are about to be treated with penicillin or semi-synthetic penicillins or cephalosporins or other $\beta$-lactam antibiotics.

The preferred new MDM consists of NaBPO, PG and BPO-propyl amine (or BPO-ethyl amine or other BPO-alkyl amines or BPO-aminoacids in accordance with my invention). I believe that elimination of the BPO-amine and POIC from previously disclosed MDM mixtures would not cause lowered sensitivity, as a combination of NaBPO and BPO-propyl amine would detect those patients. BPO-propyl amine and BPO-ethyl amine were chosen as the preferred new MDM materials because their side chains are most similar to the majority of aminoacids and amines possible in view of the compounds found in blood and plasma. (See Tables IA, IB and IC for a listing of amines and aminoacids identified as being present in human blood and plasma.) Others may be added or substituted later. Following my invention, I believe that the aminoacid residue of my new MDM materials may be selected from any of the aminoacids found in blood plasma and tissue fluids, typical of which are those illustratively set forth in Tables IA., IB. and IC, as well as 2-aminopropanoic acid, 2-aminobutanoic acid, 2-aminopentanoic acid and 2-aminohexanoic acid. These later four compounds are structurally similar to some amines and aminoacids found in blood. These N-penicilloyl amines and aminoacids may be $\alpha$-diastereoisomers, other diastereoisomers or diastereoisomeric mixtures.

TABLE I

A. Aliphatic Amines In Blood Or Plasma[1]

| Amines | Concentration (mg/liter) | |
|---|---|---|
| | Mean | Range |
| Total aliphatic amines[2] (as Nitrogen) | 0.3 | (0.08–0.52) |
| Cystamine[2] HSCH₂CH₂NH₂ | 2.9 | |
| Spermine[2] H₂N(CH₂)₃NH(CH₂)₄NH(CH₂)₃NH₂ | 1.34 | (1.14–1.54) |
| Spermidine[2] H₂N(CH₂)₃NH(CH₂)₄NH₂ | 0.96 | (0.86–1.06) |
| Phosphoethanolamine[3] $HOP(O)(OH)OCH_2CH_2NH_2$ | 0.5 | (0.0–1.1) |

[1] From "Scientific Tables", Diem & Lentner edit., 7th ed., 1970, Ciba-Geigy.
[2] Whole blood.
[3] Blood plasma.

TABLE I

B. Aminoacids In Blood Plasma[1]

| Aminoacid | Concentration (mg/liter) |
|---|---|
| Free aminoacid as $\alpha$-NH₂ nitrogen | 42 |
| Alanine | 31 |
| Arginine | 14 |
| Cystine | 18 |
| Glutamine | 83 |
| Glycine | 17 |
| Histidine | 12 |
| Leucine | 13 |
| Lysine | 25 |
| Proline | 27 |
| Serine | 12 |
| Threonine | 19 |
| Valine | 20 |

[1] From CRC Handbook of Biochemistry. The list presented here is incomplete.

TABLE I

C. Aminoacid Structures $$\begin{array}{c} COOH \\ \setminus \\ HC-R \\ / \\ NH_2 \end{array}$$

where R =

| Alanine | —CH₃ |
|---|---|
| Valine | —CH(CH₃)₂ |
| Leucine | —CH₂CH(CH₃)₂ |
| Asparagine | —CH₂CONH₂ |
| Glutamine | —CH₂CH₂CONH₂ |
| Lysine | —(CH₂)₄NH₂ |

TABLE I-continued

C. Aminoacid Structures $$\begin{array}{c} COOH \\ \backslash \\ HC-R \\ / \\ NH_2 \end{array}$$

where R =

| | |
|---|---|
| Histidine | $\begin{array}{c} HC=\!\!=\!\!C-CH_2 \\ |\quad\quad | \\ HN\quad N \\ \backslash\!\!\!/ \\ C \\ | \\ H \end{array}$ |
| Proline | $\begin{array}{c} CH_2 - CH_2 \\ |\quad\quad | \\ CH_2\quad CHCOOH \\ \backslash\!\!\!/ \\ N \\ | \\ H \end{array}$ |

The invention, with respect to my novel MDM materials, compositions and skin testing methods, will be more fully appreciated by reference to the following detailed description.

D. Preparation Of BPO-amines, e.g., N-Dα-(benzylpenicilloyl)-amine 1. n-propyl amine derivative 26 g (0.07 mole) of potassium PG was dissolved in 200 ml of water. n-Propyl amine (6.2 g or 0.105 mole) was added dropwise to the stirred penicillin solution at room temperature (25° C.) under pH control. The pH was maintained at 11.2–11.5 for about 5 minutes, during which time about 0.07 moles of n-propyl amine was added. After that, the pH rose to 11.8–12.0 as the excess of n-propyl amine was added over an additional 5 minutes. The mixture was then stirred at room temperature for an additional 60 minutes.

The resulting solution was cooled to 5°–10° C. in an ice bath, and the pH adjusted to 3.8–4.0 by additions of 3 N HCl to the stirred reaction mix. The resulting white precipitate was separated by filtration and washed extensively with cold water. The moist solid was dried under high vacuum.

y = 20 g white powder (70%).

Analysis: Calculated for $C_{19} H_{27} N_3 O_4 S.H_2O$: C55.46; H7.10; N10.21; Found: C55.34; H6.79; N10.26; $[\alpha]^{26} = +111.2°$ (C, 1.006%, 0.2 M phosphate buffer, pH 8.0).

2. n-ethyl amine derivative 37.3 g (0.10 mole) of potassium PG in 150 ml of water was treated with 6.9 g (0.15 mole) of ethyl amine in 20 ml of water added dropwise to the stirred penicillin solution over 10 minutes, as above for the propyl amine derivative. The reaction mixture was stirred for 45 minutes at room temperature, then lyophylized to give 41 g of crude material. The material was dissolved in 50 ml of 10% acetone-water, and the solution was cooled to 8° C. and adjusted to pH 3.9 with 3 N HCl. The precipitate which formed was removed by filtration and washed 3 times with ice-cold water. The moist solid was dried under high vacuum.

y = 23 g white powder (60%).

Analysis: Calculated for $C_{18} H_{25} N_3 O_4 S.1.5 H_2O$: C.53.19; H6.94; N10.34; Found: C.53.74 H6.53 N10.55. $[\alpha]^{26} = +125.0$ (C, 0.9712%, 0.2 M phosphate buffer, pH 8.0)

3. n-butyl amine and n-amyl amine derivative

These were prepared in the same way using 1.5 g of the amine per equivalent of PG with precipitation of the product from the aqueous reaction mixture of 10° C. by adjusting the pH to 3.9±0.1.

E. Preparation of N-Dα-benzylpenicilloyl Aminoacid Derivatives

N-Dα-benzylpenicilloyl derivatives of α-aminoacids and other amines and aminoacids can be prepared. These include the natural aminoacids found in human blood plasma as shown in Table I as well as:

i. α-aminopropanoic acid (2-aminopropanoic acid)
ii. α-aminobutyric acid (2-aminobutanoic acid)
iii. α-aminovaleric acid (2-aminopentanoic acid)
iv. α-aminocaproic acid (2-aminohexanoic acid) (norleucine)

These aminoacids may be D, L or DL isomers.

Penicilloyl derivatives such as indicated above can be prepared from all semi-synthetic penicillins as well as from PG. Thus, ampicillin, amoxacillin, aczlocillin, carbenicillin, napthacillin, oxacillin, cloxacillin, staphcillin, phenoxyethylpenicillin, phenoxymethylpenicillin, piparicillin, mezlocillin, etc. can be used to prepare these penicilloyl derivatives. Possibly, cephalosporins and other Δ-lactam antibiotics may be used.

The N-penicilloyl amines and aminoacids derivatives such as indicated above can be prepared as diastereoisomeric mixtures, other diastereoisomers as well as the α-diastereoisomers. The above derivatives may also be prepared by other synthetic procedures, and the isolation and purification of the final products can also be done by other procedures.

F. Skin Testing

The tests referred to above and in the following table were conducted as described below.

1. Skin test materials

Benzylpenicilloyl-polylysine (BPL) was a heterogeneous PPL preparation averaging benzylpenicilloyl$_7$-polylysine$_9$ ($B_7L_9$) at $1\times10^{-6}$ M concentration of the conjugate in trisbuffered saline at pH 8.2.

Benzylpenicillin (PG) was $1.0\times10^{-2}$ M in 0.11 M saline.

Sodium benzylpenicilloate plus sodium benzylpeniloate (P/P) was $1.0\times10^{-2}$ M of each dissolved in phosphate buffered saline at pH 7.5.

Benzylpenicilloyl-amine (BPO-amine) was $1.0\times10^{-2}$ M concentration phosphate buffered saline at pH 7.5.

Benzylpenicilloyl-n-propyl amine and benzylpenicilloyl-n-ethyl amine (as α-diastereoisomers) were each dissolved to $1.0\times10^{-2}$ M concentration in phosphate buffered saline at pH 7.5.

While aqueous solutions are described above, other suitable solvents may be used for both PPL and the MDM, e.g., 50/50 glycerol-water mixtures.

2. Patients

There were nine patients known to give positive skin tests to penicillin derivatives. They were healthy men and women ranging in age from 23 to 56 years. Ten people negative to the skin test materials served as controls.

3. Skin test procedure

Using 1.0 ml tuberculin syringes with #26 needles and intradermal bevels, 0.01 ml volumes of the test materials were injected intradermally into the anterior-lateral aspects of the arms. Skin tests were read in 15 minutes. A negative reaction is the poorly outlined bleb of fluid—1–3 mm in diameter with surrounding erythema. Positive tests were sharply outlined wheals of 4-20 mm diameter with surrounding erythema. The positive tests were graded as 1+, 2+, 3+ and 4+ on the basis of wheal diameter. 1+ =4-6 mm; 2+ =7-9 mm; 3+ = 10-12 mm; and 4+ = more than 13 mm with pseudopods. The stronger reactions had wider circles of surrounding erythema which were more intensely red. Skin tests were done in duplicate. Duplicates gave identical or nearly identical readings.

4. Test results

The results of the penicillin allergy tests conducted by the procedures reported above are set fourth in Table II.

TABLE II

| Skin Test Material | LI | DL | NT | LG | RM | HD | CM | MB | HM |
|---|---|---|---|---|---|---|---|---|---|
| (Conc.) | | | | | | | | | |
| BPL 1 × 10⁻⁶M | 1+ | 4+ | 0 | 0 | 4+ | 4+ | 0 | 3+ | 0 |
| PG 1 × 10⁻²M | 2+ | trace | 1+ | trace | 0 | 0 | 0 | 2+ | 0 |
| P/P 1 × 10⁻² | 1+ | 1-2+ | 3+ | 2+ | 0 | 1+ | 1-2+ | 2+ | 2-3+ |
| (of each ingredient) | | | | | | | | | |
| BPO-amine 1 × 10⁻²M | 1-2+ | trace | 2-3+ | 2+ | 0 | 1+ | 1+ | 1-2+ | 2-3+ |
| BPO-ethyl amine 1 × 10⁻²M | 1-2+ | trace | 1-2+ | 1+ | 0 | 1-2+ | 2+ | 3+ | 2-3+ |
| BPO-propyl amine 1× 10⁻²M | 1-2+ | trace | 2+ | 1+ | 0 | 1-2+ | 2-3+ | 3-4+ | 2-3+ |
| Diluent control | 0 | 0 | 0 | 0 | 0 | 0 | 0 | 0 | 0 |

*Ten control patients gave negative skin tests to the skin test materials.

Skin Test Reactions To BPO-amines And Other Penicillin Allergy Skin Test Materials Intensity of reactions is patients*

G. Preparation of Storage-Stable MDM Materials

The components of the MDM are unstable in aqueous solution. In order to obtain a pharmaceutical preparation with an acceptable shelf life, the MDM components of the penicillin allergy tests are lyophilized in single dose vials. The single dose lyophilized MDM is provided along with a multidose aqueous buffer, or other appropriate diluent, for reconstitution just prior to use. This diluent is used also as the material for the diluent control test.

For example, to prepare a batch of 10,000 vials of the MDM, the following is done:

15.32 gm monosodium benzylpenicilloate plus 16.08 gm benzylpenicilloyl-n-propylamine is placed into a clean and sterile 4 liter glass beaker. Three liters of cold water-for-injection is added. The mixture is stirred while 0.3 M NaOH is added to keep the pH between 7 and 9.5. When the solids are dissolved, the pH is finally adjusted to 7.2. 14.88 gm of potassium benzylpenicillin is then dissolved into this solution, the final volume adjusted to 4.00 liters with water-for-injection, and the final pH adjusted to 7.2±0.1. The cold MDM solution is sterilized by filtration through a membrane filter such as a 0.2 or 0.22 micron membrane filter. The cold sterile MDM solution is then dispensed sterile in in 0.30 ml volumes into 2 ml sterile vials, and the vials are placed into a lyophilizer.

Many lyophilization systems may be used. As an example, one system that may be used is the Virtis 250 or 500 SRC. Trays filled with the 2 ml vials containing 0.30 ml of MDM are immediately frozen at −40° C. Lyophilization at 5 microns Hg pressure may be carried out for a total of 48 hours. The temperature is kept at −40° C. for 10 hours and then raised 2° per hour until ambient temperature (approx. 25° C.) is reached. The sterile, dried vials are capped with rubber stoppers and sealed with an aluminum band. The lyophilized MDM so prepared should be stable for up to about 4 years when stored at 5°-10° C.

Those of skill in the art will be aware of other ways of practicing the above-described invention without departing from the spirit or scope of the invention as set forth in the following claims.

What is claimed is:

1. A storage-stable composition capable of being reconstituted by mixture with a suitable solvent to form a composition useful in skin testing for penicillin allergy or hypersensitivity to penicillins, including benzyl penicillin and semisynthetic penicillins, comprising an amount effective for detecting penicillin allergy or hypersensitivity of a lyophilized mixture of (1) a compound represented by the formula:

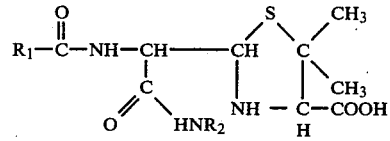

wherein:

R₁ is a side chain contained in the penicillins from which the penicilloyl amine or aminoacid compound is prepared; said penicillins being selected from the group consisting of benzylpenicillin and semi-synthetic penicillins, and R₂ is a substituent selected from the group consisting of an alkyl group of C₂–C₆ chain length, a carboxy alkyl group of C₂–C₆ chain length, and a residue of an aminoacid or amine compound of the type present in the blood, blood plasma or tissue fluids, said compound being selected from the group consisting of cystamine, spermine, spermidine, phosphoethanolamine, arginine, cystine, glutamine, histidine, lysine, proline, serine, threonine, and asparagine, said compounds being α-diastereoisomers or diastereoisomeric mixtures;

(2) benzylpenicillin; and (3) sodium benzylpenicilloate.

2. The composition of claim 1, wherein R₂ is ethyl.

3. The composition of claim 1, wherein R₂ is propyl.

* * * * *